(12) United States Patent
Vayser et al.

(10) Patent No.: US 11,622,832 B2
(45) Date of Patent: Apr. 11, 2023

(54) PROJECTION SCANNING SYSTEM

(71) Applicant: Invuity, Inc., San Francisco, CA (US)

(72) Inventors: Alex Vayser, Mission Viejo, CA (US); Dennise Dalma-Weiszhausz, Palo Alto, CA (US)

(73) Assignee: Invuity, Inc., San Francisco, CA (US)

( * ) Notice: Subject to any disclaimer, the term of this patent is extended or adjusted under 35 U.S.C. 154(b) by 292 days.

(21) Appl. No.: 16/634,051

(22) PCT Filed: Jul. 27, 2018

(86) PCT No.: PCT/US2018/044169
§ 371 (c)(1),
(2) Date: Jan. 24, 2020

(87) PCT Pub. No.: WO2019/023625
PCT Pub. Date: Jan. 31, 2019

(65) Prior Publication Data
US 2021/0145536 A1  May 20, 2021

Related U.S. Application Data

(60) Provisional application No. 62/537,627, filed on Jul. 27, 2017.

(51) Int. Cl.
*A61B 5/00* (2006.01)
*A61B 90/00* (2016.01)
(Continued)

(52) U.S. Cl.
CPC .......... *A61B 90/361* (2016.02); *A61B 5/0071* (2013.01); *A61B 90/39* (2016.02);
(Continued)

(58) Field of Classification Search
CPC ..... A61B 90/361; A61B 5/0071; A61B 90/39; A61B 2090/365; A61B 2090/395;
(Continued)

(56) References Cited

U.S. PATENT DOCUMENTS

| 7,567,833 B2 | 7/2009 | Moctezuma De La Barrera et al. |
| 2005/0195587 A1 | 9/2005 | Moctezuma De La Barrera et al. |
| | (Continued) | |

FOREIGN PATENT DOCUMENTS

| JP | 2012030042 A | 2/2012 |
| JP | 2016007396 A | 1/2016 |

OTHER PUBLICATIONS

International Search Report dated Oct. 10, 2018, issued in connection with International Application No. PCT/US2018/044169, filed on Jul. 27, 2018, 3 pages.
(Continued)

*Primary Examiner* — Joel Lamprecht
(74) *Attorney, Agent, or Firm* — McDonnell Boehnen Hulbert & Berghoff LLP

(57) ABSTRACT

Imaging systems projecting augmented information on a physical object that at a minimum include a processor, a memory device operably connected to the processor, a projector operably coupled to the processor, and a distance-measuring device operably connected to the processor. The memory device stores augmented image information, and the processor is configured to project augmented image information onto the physical object. The distance-measuring device is configured to measure the distance to the physical object. The processor uses distance measurement information from the distance measuring device to adjust scaling of the augmented image information. The processor provides the scale adjusted augmented image information to the projector. System can also be used for fluorescence imaging during open surgery, for endoscopic fluorescence imaging and for registration of surgical instruments.

23 Claims, 4 Drawing Sheets

System 100

(51) Int. Cl.
  *G01P 13/00*       (2006.01)
  *G01S 17/08*       (2006.01)
  *H04N 5/232*       (2006.01)
  *H04N 9/31*        (2006.01)

(52) U.S. Cl.
  CPC .............. *G01P 13/00* (2013.01); *G01S 17/08* (2013.01); *H04N 5/23251* (2013.01); *H04N 9/31* (2013.01); *A61B 2090/365* (2016.02); *A61B 2090/395* (2016.02)

(58) Field of Classification Search
  CPC ... A61B 90/36; A61B 2090/366; G01P 13/00; G01S 17/08; H04N 5/23251; H04N 9/31; G02B 2027/0127; G02B 2027/0138; G02B 2027/014; G02B 2027/0141; G02B 27/017
  See application file for complete search history.

(56) References Cited

U.S. PATENT DOCUMENTS

| | | |
|---|---|---|
| 2011/0320153 A1* | 12/2011 | Lightcap ............... A61B 34/20 702/94 |
| 2012/0268573 A1 | 10/2012 | Schonborn et al. |
| 2013/0060146 A1* | 3/2013 | Yang ..................... G01B 11/25 600/476 |
| 2013/0300637 A1 | 11/2013 | Smits et al. |
| 2015/0261497 A1 | 9/2015 | Poulad et al. |
| 2016/0242934 A1 | 8/2016 | van der Walt et al. |
| 2017/0086940 A1 | 3/2017 | Nakamura |
| 2017/0165028 A1 | 6/2017 | Hummelink |

OTHER PUBLICATIONS

Written Opinion dated Oct. 10, 2018, issued in connection with International Application No. PCT/US2018/044169, filed on Jul. 27, 2018, 6 pages.

* cited by examiner

PROJECTION SCANNING SYSTEM

CROSS-REFERENCE

This application is a U.S. National Phase Application under 35 U.S.C. § 371 of International Application No. PCT/US2018/044169, filed Jul. 27, 2018, which claims the benefit of U.S. Provisional Application No. 62/537,627, filed Jul. 27, 2017, which applications mare entirely incorporated herein by reference.

BACKGROUND

The present application generally relates to medical systems, devices, and methods, and more particularly relates to surgical imaging and projection.

Oftentimes, it can be challenging to present visual information to a surgeon during a surgical procedure. For example, visual information presented on an external monitor may require the surgeon to disrupt his or her focus on a surgical site to view the external monitor, and vice versa. This may be undesirable such as when the surgeon would prefer to intake the visual information whilst maintaining focus on the surgical site, or when the surgeon is otherwise unavailable to remove his or her gaze from the surgical site.

SUMMARY

Disclosed is an improved surgical imaging and projection system. The system of the present invention provides augmented information by projecting visual data onto a target. The system of the present invention includes a feedback loop that automatically adjusts the scale of the projected visual information to match the scale of the target. In some embodiments, the system detects a fiducial on the target and registers the projected visual information with the target using the location of the fiducial. The system is particularly useful for projecting additional surgical information onto a surgical site. The projected visual information may also be termed augmented or false color image, and is projected onto and registered with the real object such as a surgical site.

Many video image processing systems, such as X-ray, ultrasound, MRI or fluorescent systems are used during surgery. These image systems typically utilize a monitor to provide the surgeon with additional information. Although this information is helpful, viewing this additional data requires the surgeon to shift his/her field of view between the surgical field and a monitor. The present invention discloses embodiments for projecting the augmented image information directly onto the patient (surgical field). The augmented image information can be CT images (computerized axial tomography), MRI images (magnetic resonance imaging), fluorescence information or the like. This enables the surgeon to maintain his/her view of the surgical field and is completely intuitive.

According to one embodiment a false color image (in the visible light spectrum), corresponding to an augmented image (e.g., fluorescent image or MRI image), is projected directly onto the patient (surgical field). This enables the surgeon to "see" the augmented image without the use of special equipment (e.g., goggles) while maintaining their field of view on the surgical field. However, one of the embodiments disclosed herein includes a head mounted display, which may be advantageous in certain settings.

One of the problems that has prevented the projection of augmented image information in a surgical setting relates to scaling and registration of the augmented image relative to the three dimensional human anatomical structures. When the camera/projector is at a specific distance relative to the surgical field it will image and project a picture at a specific magnification. It is critical that the projected image is registered with the actual real anatomical object, i.e., size and orientation. This may be easily optimized for a fixed, known distance to adjust the magnification of the projected image. However, the issue arises when the distance or orientation of the camera changes from that optimized position. If the camera moves further away from the object, the object will appear smaller to the camera and thus the scale of the image projected will be smaller than the real object.

The embodiments disclosed herein monitor the distance and orientation of the projector relative to the target (e.g., patient or real object) in real time and automatically adjust the magnification/scaling of the projected image.

Another problem that has prevented the projection of augmented image information in a surgical setting relates to the orientation of the camera relative to the body. The perceived shape of the real object will differ depending on the viewing angle. It is critical that the orientation of the augmented image match the orientation of the real object.

It would be useful to provide intuitive real-time visual feedback to the user on how to adjust the orientation of the system for optimal results.

In another part of the invention, the ability to measure distance, orientation and the actual target topology can create significant benefits in systems that require high sensitivity to signal. For example, in fluorescence imaging, the goal is to create an imaging system with a large aperture to collect as much emission light as possible (to maximize sensitivity). Doing so creates a challenge because generally a large aperture system suffers from very short depth of focus. When the camera in such a system moves beyond the range of the depth of focus, the lens must be refocused. This can be resolved by placing a variable focal lens in the optical train, more specifically, it is ideal to use electrically tunable lenses. Continuous monitoring of the physical distance between the camera and the physical object in real time allows the system to adjust the focal length of the variable length lens (in real time) while maintaining the aperture as large as possible. It is highly desirable to have the auto-focusing occur without any visible delay (as commonly seen with traditional mechanically driven focusing systems) as to minimize the image quality deterioration.

Specifically for fluorescence, the system is able to monitor the intensity signal based on distance between the camera and the target. Therefore, the system can be calibrated to quantify the amount of pixel intensity based on emission (fluorescence) signal. As will be appreciated, the intensity of the fluorescent signal varies with distance. The shorter the distance (closer the system is to the fluorescing object), the more intense the emission signal. The system may be able adjust the gain of the signal in relation to the measured distance. If the emission signal is weaker than expected for a given distance then the system may determine that there is an issue requiring further attention.

Yet another problem, which has prevented the projection of augmented image information in a surgical setting, relates to focus across a broad area. The human body is not, for the most part, planar. The topology of the human body makes it difficult to keep multiple planes in focus. The present invention discloses several approaches for measuring the topology of the physical object, which may facilitate keeping each of the planes in focus.

In an aspect, provided is an imaging system projecting augmented information on a physical object, the imaging system comprising: a processor; a memory device operably connected to the processor, the memory device storing augmented image information; a projector operably coupled to the processor, the processor configured to project augmented image information onto the physical object; and a distance-measuring device operably connected to the processor and configured to measure the distance to the physical object, the processor using distance measurement information from the distance measuring device to adjust scaling of the augmented image information, the processor providing the scale adjusted augmented image information to the projector.

In some embodiments, the distance-measuring device is selected from the group consisting of laser range finder, laser scanning, time of flight, structured light, light field camera, and acoustic measurement device.

In some embodiments, the distance-measuring device further determines at least one of a topology of the physical object and an orientation of the physical object relative to the distance-measuring device, and the processor further uses the topology and/or orientation information to adjust scaling of the augmented information.

In some embodiments, the imaging system further comprises at least one light source selected from the group consisting of structured light, background infrared light, visible light, and fluorophore excitation light.

In some embodiments, the distance measuring device comprises: at least one of an sensor and a camera operably connected to the processor, wherein the at least one light source includes a source of structured light configured to project a predefined light pattern onto the physical object in at least one of a visible and an infrared light spectrum, and wherein the at least one of a sensor and a camera detect a reflectance of the predefined light pattern and the processor calculates at least one of the distance to the physical object and a topology of the physical object using the detected reflectance.

In some embodiments, the distance measuring device comprises: at least one of a sensor and a camera operably connected to the processor, wherein the projector is configured to project a predefined light pattern onto the physical object in at least one of a visible and an infrared light spectrum, and wherein the at least one of a sensor and a camera detect a reflectance of the predefined light pattern and the processor calculates at least one of the distance to the physical object and a topology of the physical object using the detected reflectance.

In some embodiments, the projector projects at least two predefined light patterns onto the physical object and the at least one of a sensor and a camera detect a reflectance of the at least two predefined light patterns and the processor calculates at least one of the distance to the physical object and a topology of the physical object using the detected reflectance.

In some embodiments, the at least one of a sensor and a camera are further configured to detect a location of a fiducial attached to or painted onto the physical object, the fiducial being visible in either a visible light spectrum or an infrared spectrum, the processor using the location of the fiducial to register the augmented image information with the physical object.

In some embodiments, the distance measuring device comprises a time of flight sensor unit including a light source and a sensor. In some embodiments, the light source is an infrared capable light source and the light sensor is capable of detecting infrared light.

In some embodiments, the distance measuring device comprises: at least one of a sensor and a camera operably connected to the processor; and a second projector, said second projector configured to project at least one predefined structured light pattern in either a visible or infrared spectrum onto the physical object, wherein the at least one of a sensor and a camera detect a reflectance of the predefined light pattern, the processor calculates at least one of the distance to the physical object and a topology of the physical object using the detected reflectance and uses the calculated distance and/or topology to adjust scaling of the augmented information, the processor providing the scale adjusted augmented information to the projector.

In some embodiments, the at least one of a sensor and a camera are further configured to detect a location of a fiducial attached to or painted onto the physical object, the fiducial being visible in either a visible light spectrum or an infrared spectrum, the processor using the location of the fiducial to register the augmented image information with the physical object.

In some embodiments, the imaging system further comprises an IMU operably connected to the processor.

In some embodiments, the processor disables the distance-measuring device from making distance measurements if the IMU detects that the imaging system is stationary for at least a predefined amount of time.

In some embodiments, the processor disables the projector from projecting if the IMU detects that the imaging system is moving more than predefined threshold amount or misoriented.

In some embodiments, the processor triggers the projector to display an alert if the imaging system is not oriented within predefined threshold.

In some embodiments, the processor triggers the projector to display an alert if the measured distance to the physical object exceeds a predefined threshold distance.

In some embodiments, the imaging system further comprises a light, wherein the processor disables the light if the IMU detects that the imaging system is moving more than predefined threshold amount or misoriented.

In some embodiments, the imaging system further comprises: at least one of a camera or sensor operably connected to the processor and configured to detect a fluorescent emission, the processor causing the projector to project light to excite fluorophores in or on the physical object, and the camera or sensor detecting a fluorescent emission of the fluorophores, the processor storing the detected fluorescent emission in the memory as augmented image information.

In some embodiments, the projector projects the augmented image information onto the physical object using light in the visible spectrum.

In some embodiments, the projector has a first mode for projecting augmented image information on the physical object, and second mode for projecting light to excite fluorophores in or on the physical object. In some embodiments, the projector has a third mode for projecting a predefined light pattern.

In some embodiments, the projector is capable of projecting light in both a visible and an infrared light spectrum.

In some embodiments, the imaging system further comprises: at least one of a camera or sensor operably connected to the processor and configured to detect a fluorescent emission; and at least one of a light source and a second the projector configured to project light onto the physical object, the processor causing the at least one of a light source and a second projector to project light to excite fluorophores in or on the physical object, and the at least one of a camera or sensor detecting a fluorescent emission of the fluorophores, the processor storing the detected fluorescent emission in the memory as augmented image information.

In some embodiments, the processor triggers the projector to display an alert if an intensity of the detected fluorescence is below a threshold value.

In some embodiments, the imaging system further comprises: at least one of a camera or sensor operably connected to the processor; and a second the projector operably connected to the processor and configured to project a virtual fiducial in either an infrared light or visible light spectrum onto the physical object, the processor causing the second projector to project the virtual fiducial on the physical object, the camera or sensor detecting a location of the virtual fiducial, and the processor using the location of the virtual fiducial to register the augmented image information with the physical object.

In some embodiments, the memory is operably connected to the processor using a remote communications protocol.

In some embodiments, the augmented image information is projected in the visible light range.

In some embodiments, the imaging system further comprises: at least one of a camera or sensor operably connected to the processor and configured to detect fluorescent emission, the processor causing the projector to project light to excite fluorophores in or on the physical object, and the camera or sensor detecting a fluorescent emission of the fluorophores in a first wavelength, the processor storing the detected fluorescent emission in the memory as augmented image information and triggering the projector to project the augmented image information onto the physical object in a second wavelength different from the first wavelength.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
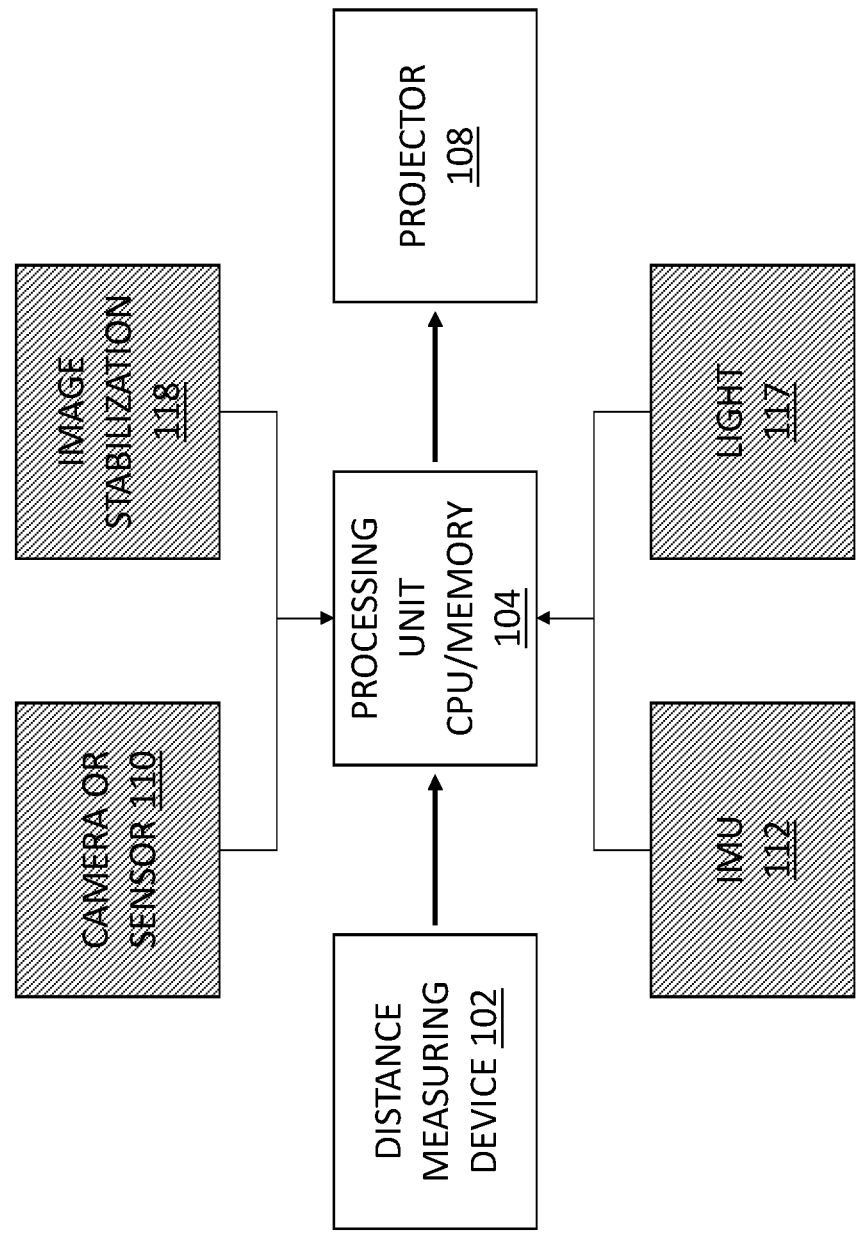
FIG. 1 shows a block diagram of an augmented imaging system.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

As noted above, the invention is useful in providing augmented visual information from any source including but not limited to ultrasound, x-ray, CT scan, fluorescence imaging or the like.

Augmented Information Projection

The invention is useful in projecting augmented information onto a physical object. The phrase "physical object" is intended to include the patient and the surgical site, but is not so limited. In order for the augmented information to be truly useful, it must be precisely registered with the physical object. In other words, the alignment, the scale and orientation must match the position and scale of the physical object onto which it is projected. Better yet, the augmented image can be digitally altered to compensate for the orientation and/or topology of the physical object.

The present invention contemplates several different ways to measure the distance between the projector and the physical object, which are explained at length below. Some of these distance-measuring techniques also yield the orientation and/or topology/contour of the physical object. The system of the present invention uses the calculated contour and/or distance to scale the augmented information so that it corresponds to the scale of the physical object.

The augmented information may be saved or transmitted to the system wirelessly or over a data cable. The wireless communication may use Bluetooth, WIFI, or any other communication protocol.

Measuring the Distance Between the Camera or Projector and the Physical Object

A conventional laser range finder (distance sensor) may be used to measure the distance between the projector and the physical object. The laser shines light on the physical object and a sensor detects how much time it takes for the light to be reflected back. It is straightforward to calculate the distance between the object and the laser emitter given the time it takes for the reflectance to reach the sensor and the speed of light. This technique is useful but not ideal since it does not provide information regarding the contour/topology of the physical object in the field of view of the camera. One example of a commercial laser range finder is LIDAR-Lite by Garmin International, Inc., 1200 E. 151st St., Olathe, Kans. 66062-3426. There are two different mechanisms by which distance sensors measure the distance to an object, time of flight or triangulation. These two mechanisms can be achieved with either a laser or an LED as the light source.

Techniques for Measuring the Contour/Topology

There are various ways to capture 3D topology of objects. The classic way utilizes a stereo setup where a pair of cameras is used to capture two different points of view. Next, image processing is used to reconstruct the image into a 3D depth map. This strategy does not work well when there is a lack of contrast; it is also hardware and software intensive and is not commonly used due to its complexity.

This classic process has now evolved into four configurations: Laser Scanning, Time of flight, Structured Light, and Light Field. Each of these techniques are applicable to the present invention. The differences between these techniques are as follows:

1) Laser Scanning typically uses a single camera and a laser-projected line. This system requires relative movement between the object and the laser-projected line. So either the laser projected line is scanned (moved over the object) or the object is displaced to create the relative movement. As the line becomes distorted due to the topology of the object, the camera picks up the deformation and reconstructs the shape of the object. This is the most accurate way to scan the object, but requires either the object or the imaging system to move, which may not be practical for static applications.

2) Time of Flight (TOF) imaging sensors are commercially available. Three-dimensional (3D) time of flight imaging sensors operate by illuminating an area with modulated IR light pattern. By measuring the phase change of the reflected signal the distance can be accurately determined for every pixel in the sensor creating a 3D depth map of the subject, scene or object. There are various companies producing time of flight cameras and sensors such as Texas Instruments, Intel, etc. This is an excellent method to determine the position of objects as well as local depth. However, this method is only accurate to within few millimeters and is sensitive to ambient light. So is not as accurate outdoors, for example.

3) Structured Light uses a predefined pattern or more preferably a series of predefined patterns, which are projected onto an object. The pattern(s) may or may not be visible to the unaided human eye, e.g. IR pattern. The camera compares the projected pattern against the detected pattern and determines the distance and contour/topology of the object from the deformation of the detected pattern compared to the original projected one. The optimal method to do this is to project various patterns to increase the resolution of the depth map. The structured projection is an excellent way to scan objects with accuracy and efficiency.

4) Light Field Cameras, also known as plenoptic cameras, capture information about the light field emanating from a scene; that is, the intensity of light in a scene, and the direction that the light rays are traveling in space. This contrasts with a conventional camera, which records only light intensity. One type of light field camera uses an array of micro-lenses placed in front of an otherwise conventional image sensor to sense intensity, color, and directional information. Multi-camera arrays are another type of light field camera.

FIG. 1 represents a block diagram of the basic embodiment of an augmented imaging system 100 according to the present invention. The unhashed blocks, represent this basic embodiment, while hashed blocks depict the functionalities that are optional. The augmented imaging system 100 includes a distance-measuring device 102, a processing unit 104, and a projector 108. In this basic embodiment, processing unit 104 uses the distance information from the distance-measuring device 102 to adjust the scale of the augmented image information and then direct that information to the projector 108. The projector then projects the scaled augmented image onto the object.

Device 102 is composed of an emitter and a receiver for distance or topology measurement. It can include a variety of emitting and detecting modalities and components such as acoustics, triangulation and range finder lasers, laser scanning, photodetectors and TOF. The specific way the distance is measured is not critical as long as it is accurate. The processing unit 104 includes image processing power, memory and lookup tables. The projector 108 may be a three-color (RGB) laser, an IR laser or an LED projector. Projector 108 can project continuously or intermittently in visible or IR and can also provide structured light in visible or IR. Furthermore, projector 108 can also alternate between augmented image and structured light. A DLP projector may also be used but such a projector may not provide optimal results. A laser projector is particularly advantageous because it can utilize the distance information to optimally focus the augmented image projection in multiple planes.

In some embodiments, the augmented information is transmitted wirelessly to the augmented imaging system 100. Any wireless communications protocol may be used. Such wireless communications protocol may include Bluetooth, WiFi, or the like. The augmented information may be any information from any source. In a surgical setting, the augmented information may be any information useful to the surgeon and may include a CT scan, MRI image, X-ray, ultrasound, fluorescence or other information useful to the surgeon such as information for orienting a surgical tool.

In some other embodiments, distance sensor 102 may be used for measuring the topology/contour of the object or surgical site. As an alternative to distance sensor 102, system 100 may include the use of structured light to measure the distance and/or topology of the object and at least one detector or a camera 110. Sensor/camera 110 could be a video IR, visible or hyperspectral sensor, it could also be a TOF or an acoustic sensor. In this embodiment, one or more predefined patterns are projected on the physical object by projector 108. A sensor/camera 110 detects the projected pattern, and the processing unit 104 compares the projected pattern with the detected pattern to determine the topology/contour of the physical object. As mentioned above, this embodiment would allow not only the topological characterization, but also the assessment of the distance from the camera/sensor 110 or projector 108 to the physical object.

Projector 108 Provides Structured Light

The structured light pattern may be projected in a visible light spectrum (visible to the unaided human eye) or an IR spectrum. Moreover, the structured light may be projected using a projector 108, which in some embodiments is a visible light projector. In other embodiments, the structure light is projected in an IR spectrum using projector 108 that may be capable of projecting in both a visible light spectrum and IR. That is, both visible and IR light-emitting sources may be provided on the same module of projector 108, and both emitting sources are scanned using the same micromirror. Alternatively, projector 108 may be used to project the false color augmented images in the visible light spectrum and another projector may be used to project the structured light either in visible or in the IR spectrum.

It is also possible to use projector 108 to project both augmented image information and structured light by polling or switching between an augmented image mode and a structured light mode. In the augmented image mode, projector 108 projects an augmented (false color) RGB image onto the physical object. In the structured light mode, the projector 108 will project one or more pre-determined structured light pattern(s) onto the object. These structured light patterns may be projected in an IR spectrum or in a visible light spectrum.

Dedicated Structured Light

To reduce the burden on projector 108, it may be desirable to utilize a dedicated source of structured light. In such an embodiment, the projector 108 may be utilized to project the augmented image information onto the physical object. A dedicated source of structured light 117 may be utilized to project one or more pre-defined patterns of light onto the physical object. Structured light 117 may include a diffractive optical element or a holographic film. This dedicated light source can produce pre-defined patterns in visible or IR spectrum.

Additional Components for Topology Assessment

It should be noted that the distance measurement and topology can be obtained in a variety of ways. For example, distance measuring can be accomplished by utilizing a distance sensor 102 that contains a laser beam and sensor in one single compartment. Alternatively, it is also possible to measure the distance by using the projector 108 or light source 117 to project a signal or a pre-defined pattern in visible or IR and use sensor/camera 110 to assess the distance.

In any of the embodiments described herein, the distance-measuring device 102 may utilize a time-of-flight sensor module. The distance measuring device may also utilize a TOF sensor 110 that may be operably connected to the processing unit 104 in conjunction with a source of structured light such as projector 108 or light source 117. The projector 108 or structure light source 117 projects a structured light pattern and the TOF sensor 110 measures the phase change of the reflected signal for every pixel in the sensor creating a 3D depth map of the object (topology) and provides this information to the processing unit 104. The processing unit 104 uses image processing and the measured topology to register the image and adjust the magnified/augmented image to properly project with correct magnification and orientation.

The processing unit 104 uses the determined topography information to adjust the projection magnification of the augmented image information projected by projector 108.

Distance measurement is not limited to laser light signals. Likewise, the topological characteristics of an object can be assessed using different hardware combinations, including, for example, using the projector 108 or light source 117 to project a structured light image and the sensor/camera 110 to capture the deformation of the pattern produced by the object.

It is also possible to use structured light to determine the distance between the system and the physical object. In other words, structured light may be used to determine the topology of the object, orientation and the distance. In such an embodiment, the components used to determine topology also serve as the distance-measuring device 102. Measuring the distance between the system and the physical object, can be used to adjust the focus of camera/sensor 110.

The structured light pattern may also be useful in determining the relative orientation between the system and the real object (skew angle). The camera/sensor 110 picks up the reflectance of the structured light pattern(s) and the processing unit 104 compares the reflected pattern with the projected pattern and determines the orientation of the camera/projector relative to the real object and utilizes signal processing to adjust the visible projection to match the orientation of the camera. The processing unit 104 may be used to either store or buffer the augmented image information, and may be connected to the system using a data cable or may be wirelessly interfaced using WIFI, Bluetooth, or the like.

The above-described system may be attached to a stationary mount; however, the system is particularly useful as a hand held device because of its ability to automatically and in real-time measure and compensate for the distance and orientation of the system relative to the object onto which the augmented information is being projected. The handheld system of the present invention may be used as needed at various times during a surgical procedure. As such, there is likely to be some need for image stabilization as the camera is moved. In such a system, an optional stabilization module 118 may be added.

The augmented imaging system 100 of the present invention is preferably handheld. System 100 may optionally be enhanced by the inclusion an inertial measurement unit (IMU) 112 which may contain one or more motion and/or orientation sensor(s) such as accelerometers, gyros, and magnetometers. It may be desirable to include the IMU 112 operably coupled with the processing unit 104 to shut-off the projector(s) 108, or the distance/topology measuring device 102 when the detected system orientation deviates from an established range.

Fluorescence Imaging System 200

Figure 2:
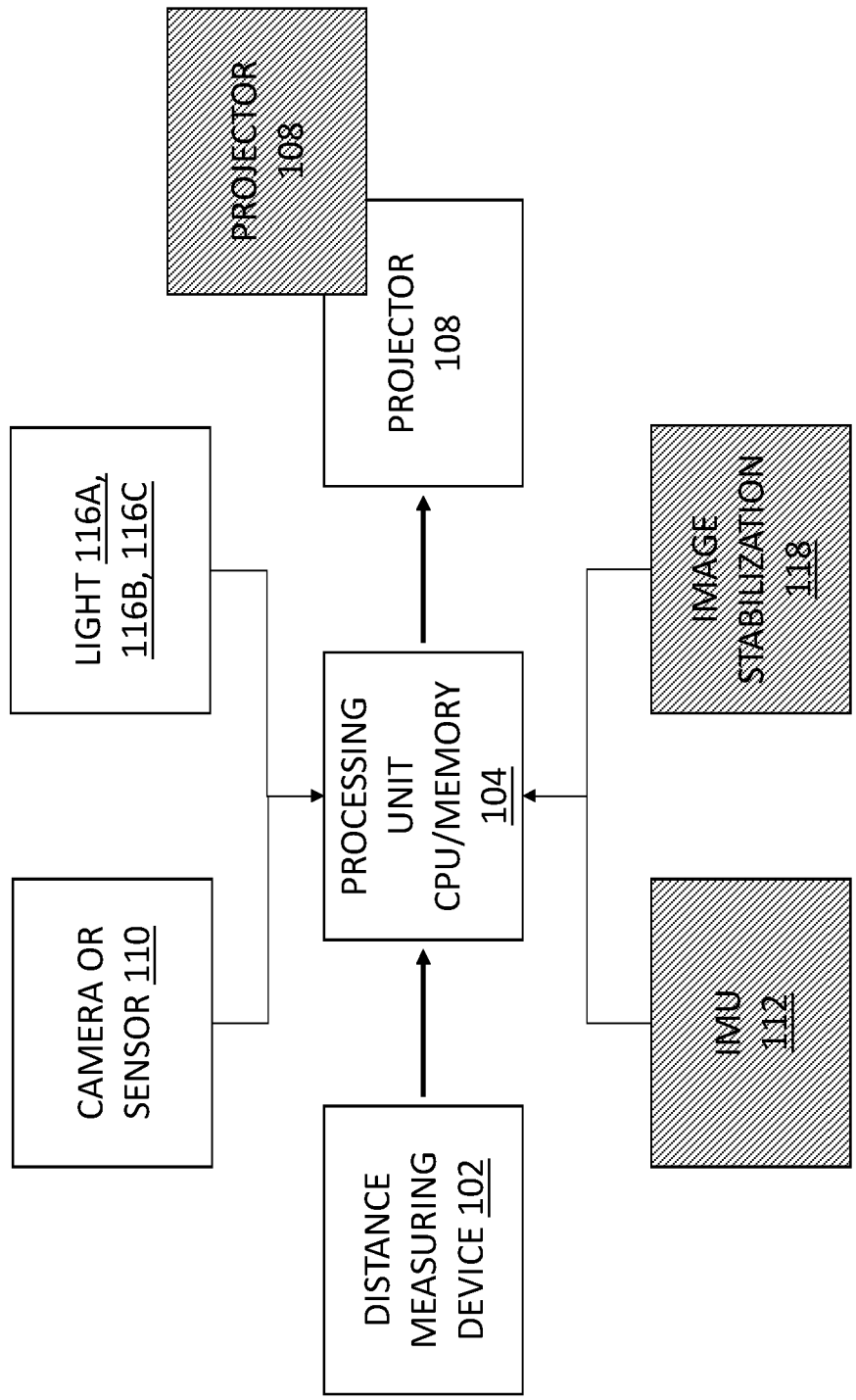
FIG. 2 shows a block diagram of a fluorescence augmented imaging system.

The augmented image projection system is particularly suited for use with a fluorescence imaging system. FIG. 2 is a block diagram of fluorescence augmented imaging system 200. Like reference numbers are intended to correspond to the same structures. Unhashed blocks refer to the basic system configuration while hashed blocks refer to optional elements. Distance measuring device 102 may utilize structured light, a TOF sensor, an acoustic sensor, a laser scanner, or a laser range finder or the like as described above with reference to FIG. 1. As will be explained below in further detail, system 200 may optionally include an additional projector 108 that may project in an infrared spectrum, visible or in both an infrared and visible light spectrum.

The system 200 may be equipped with four different and optional light sources as follows:

1) Background Illumination (116A)—The system 200 may include light source 116A to provide background illumination in an IR spectrum.

2) General Illumination (116B)—The system 200 may include light source 116B to provide general illumination in a visible light spectrum.

3) Fluorescent Excitation (116C)—The system 200 may include light source 116C to excite fluorophores. Light source 116C may illuminate in either a visible or IR spectrum depending on the specific needs of the fluorophores which will be explained in detail below.

4) Structured Light (117)—Similarly to System 100, system 200 may include light source 117 to provide the structured light pattern(s) in either a visible or IR spectrum. It should be understood that light source 117 could eliminate the need to have projector 108 project the structured light pattern(s).

The system in FIG. 2 may optionally include an additional projector 108 and any combination of light sources 116A, 116B, 116C and 117. It may be desirable to include an IMU 112 operably coupled with the processing unit 104 to shut-off the projector(s) 108, and/or light source(s) 116A, 116B, 116C, 117 when the detected system orientation deviates from an established range.

The IMU 112 can also be used to selectively deactivate/reactivate the distance monitoring process. For example, if the motion sensor detects that the system 200 is being held in a fixed or rigid manner (e.g. on a stand), the IMU 112 can disable the distance measurement process. If and when the IMU 112 detects that the system has moved then the processing unit 104 may resume the distance measurement process. This would eliminate unnecessary processing.

It may beneficial to have a fluorescent imaging system that is hand-held. Similar to system 100, system 200 may require image stabilization in which an optional module 118 is included.

System 200 is configured to excite either intrinsic, naturally occurring fluorophores, or extrinsic, those that may be added, either by infusion or by painting them onto the surface of the object. By manner of example, indocyanine green is a fluorophore approved for human use and is available under the trade name IC-GREEN®. IC-GREEN® is a water soluble, tricarbocyanine dye with a peak spectral absorption around 800 nm. Some fluorophores may be configured to bind to a particular group of cells and may be used to determine whether an area is adequately perfused, identify lesions, blood vessels, or the like.

Some fluorophores are excited by light within the visible spectrum and emit in either a visible or IR spectrum. Other fluorophores are excited by infrared (IR) light and emit in either an IR or visible spectrum, the latter through photon up-conversion.

The general principle is the same regardless of which type of fluorophore is used. Namely, the fluorophores are excited using a light source, the emission of the fluorophores is detected, and an augmented or false color image of detected emission is projected onto the physical object. In the case where the fluorophore emits in the visible range, the image information may be enhanced, as with false color, to provide additional information.

If the fluorophores are excited by light in an IR spectrum then a projector 108 or light source 116C may be used to provide the IR used to excite the fluorophores.

If the fluorophores are excited by light in a visible spectrum then projector 108 or light source 116B may be used to provide the visible light used to excite the fluorophores.

If the fluorophores emit in the IR spectrum then an IR-capable camera/sensor 110 picks up the fluorescent emission signal that is invisible to the unaided human eye and the background illumination signal (if used), and stores this data in memory, processor 104. Projector 108 projects a visible light (false color) or augmented representation corresponding to the fluorescent signal onto the real object.

If the fluorophores emit in the visible spectrum then a visible light/IR or hyperspectral capable camera/sensor 110 picks up the fluorescent emission and the background IR illumination (if used) signals. The emission intensity and background information are processed by the processing unit 104, and stored as augmented/enhanced image information. Projector 108 can then project a visible light (false color) image corresponding to the processed/augmented fluorescent emission onto the real object.

Thus, in some embodiments camera/sensor 110 is an IR capable sensor, in other embodiments camera/sensor 110 is a visible light capable sensor, and in yet other embodiments camera/sensor 110 is a capable of detecting both visible and IR light, e.g., a multispectral or a hyperspectral camera which can image both visible and IR. In yet another embodiment camera/sensor 110 is the combination of two different sensors, one that is more sensitive to visible wavelength signals, and one that is more sensitive to IR signals.

In embodiments using IR to excite the fluorophores, a bandpass filter (not illustrated) may be utilized to improve the signal to noise ratio by filtering out the wavelength of the IR light projected onto the object. More particularly, the wavelength of IR used to excite the fluorophores is different from the wavelength of the fluorescent emission of the excited fluorophores. The bandpass filter may be used to filter out the wavelength of the IR used to excite the fluorophores so that the camera only sees the wavelength of the fluorescent emission of the excited fluorophores.

If the fluorophores emit in the visible light spectrum then camera/sensor 110 picks up the emission signal. The distance sensor 102 assesses the distance between the camera/sensor 110 and the fluorescing object. The processing unit 104 can then manipulate the emission signal information as well as the distance and direct the projector 108. Projector 108 projects this visible light processed image (false color) onto the physical object but in a different visible spectrum that will not interfere with the wavelength of the emission of the visible light fluorophores. Thus, the camera 110 will use a filter (not illustrated) when capturing the emission of the visible light fluorophores to filter out the wavelength used to project the augmented image information.

The imaging system 200 may further include the capability of measuring the intensity of the fluorescence. The low intensity of the fluorescence may be due, for example, to the system being too far away from the fluorescence emission, i.e. the physical object being imaged. The imaging system 200 can gauge the distance to the object with the utilization of the distance sensor 102. The intensity of the fluorescence detected by the camera/sensor 110 will increase as the system 200 is brought closer to the physical object. Correspondingly, the intensity of the fluorescence will decrease as the system 200 is moved farther from the object. If the system 200 is positioned too far away from the object the intensity of the fluorescence will degrade below an acceptable threshold and the system will provide an alert to the user to bring the system closer to the object. The alert can be audible and/or visual. For example, the system 200 can project a warning directly on the object instructing the user to bring the system closer.

The system 200 may further include, within processing unit 104, a look-up table including the ideal threshold fluorescence intensity values as a function of distance. The system 200 can sense the distance to the physical object using, for example, distance sensor 102. If the measured fluorescence intensity is below the ideal threshold IR intensity value for the measured distance this problem may be due to low fluorophore concentration. In that case, the user may need to apply additional fluorophore to the physical object. The system 200 can also adjust the intensity of the excitation source being used to determine whether that will enhance the detected fluorescent emission intensity.

Fiducial Targets and Head Mounted Display

In any of the embodiments described herein, it may be useful to have one or more fiducial targets attached to one or more landmarks (e.g., anatomical landmarks) on the physical object on which the augmented information is being displayed. Such fiducial targets are useful for making sure that the augmented image is aligned (registered) with the object onto which it is projected. The target(s) may be physically attached to the object using any of a variety of known means including: an anchor inserted into the object, a belt, adhesive, sutures or the like. The target(s) may also include preprinted stickers, or preprinted 3M™ Ioban™ incise drapes that include the fiducial targets. It is also possible to draw the fiducial target directly on the subject/object using, for example, fluorescent ink.

The fiducial target may include a pattern visible to the unaided human eye, or the pattern may be printed using infrared ink, which is only visible to an IR capable camera, IR sensitive sensor or the like. The IR fiducial target has an advantage in that it will not interfere with the augmented image projected onto the object. It is also possible to project a virtual fiducial pattern onto the object. The virtual fiducial target may be projected using a visible light spectrum or more preferably using a light spectrum not visible to the unaided human eye, e.g., infrared light so as not to interfere with the augmented image. If the fiducial is detected in the IR spectrum, care should be taken to ensure that the IR frequency(s) used to excite the fiducial do not interfere with the IR emission frequencies of the fluorophores.

The fiducial target may be projected using the same projector 108 used to project the augmented or false color image onto the object or can be produced with structured light source 117, and it would be detected by either camera/sensor 110 or the head mounted display 120 described below for system 300. In an embodiment where the fiducials are projected by projector 108, the processing unit 104 would poll the projector 108 such that it would alternate between projecting the augmented image information and projecting the fiducial target. Using the same projector 108 to project the fiducial target and the augmented image eliminates the need to correct for misalignment between two distinct projectors.

There are various reasons why it may be advantageous to use two separate projectors, with one projector 108 for projecting the fiducial target and another projector for projecting the augmented image. In such a system, image processing may be required to bring the two projectors into alignment.

As noted above, the fiducial marker or target may be projected in a light spectrum not visible to the unaided eye, e.g., infrared (IR). This is advantageous in that the target will not interfere with the augmented or false color image projection.

Regardless of whether the fiducial target is printed/attached or projected, a custom patient-specific fiducial target can be utilized. The patient-specific fiducial contains information that would be kept private and can only be deciphered by the camera/software of the imaging system.

Figure 3:
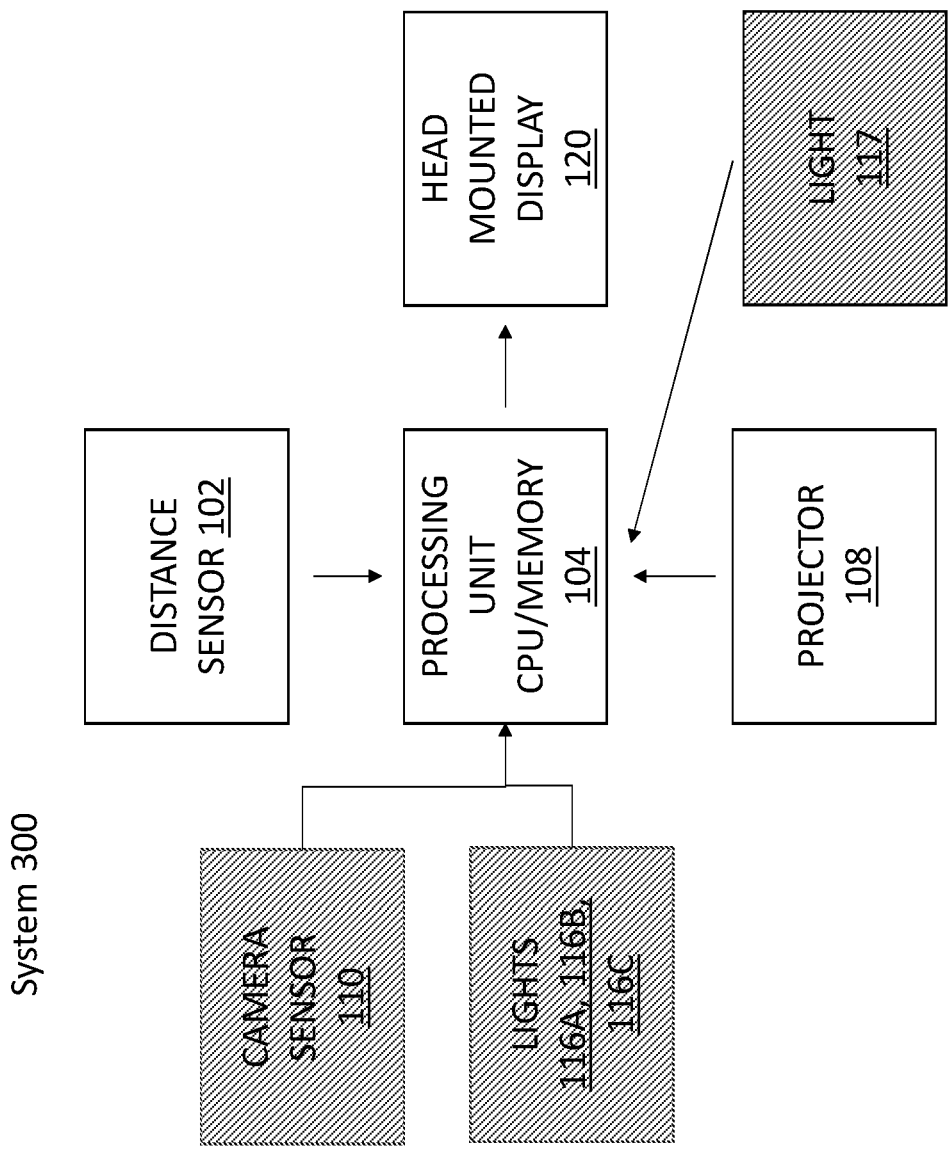
FIG. 3 shows a block diagram of a head mounted display imaging system.

FIG. 3 is a schematic diagram of a head mounted imaging system 300 in which the augmented image information is projected onto a head mounted display 120. The head mounted display has integrated sensors including imaging and inertial sensors, such as the Hololens from Microsoft. System 300 is substantially similar to system 200 (FIG. 2) but here the augmented information is displayed on the head mounted display 120 rather than being projected onto the object.

System 300 may include a distance-measuring device 102 as described above (or calculates the distance using structured light as described previously), a processing unit 104 receiving distance information from the distance measuring device 102, and processing and managing the augmented image, and a projector 108. In this embodiment, the projector 108 may be used to project a virtual fiducial onto the object rather than augmented information. Alternatively, a fiducial may be attached to or painted onto the physical object. The fiducial may be created in an IR pattern invisible to the unaided human eye by structured light source 117 or may be a visible target. In this embodiment, the user wears a head mounted display 120 equipped with a camera sensor 110 to detect the fiducial. The augmented image information is displayed on the head mounted display 120. The fiducial is used for registration of the augmented image information and to identify to the head mounted display the location in which to display the augmented image information. The augmented image is displayed on the head mounted display and thus is visible only to the user. In such an embodiment, the camera sensor 110 on the head mounted display detects the fiducial, registers the augmented image with the fiducial and displays an appropriately scaled augmented image on the head mounted display 120 to coincide with the location of the target.

It should be noted that as described above with reference to FIG. 2, the system 300 may optionally be equipped with light sources 116A, 116B and 116C.

Registration of Surgical Instruments

The augmented imaging system of the present invention can also be used for navigation/registration of surgical instruments. This system can include a distance/contour measuring device 102 as described above, a processor 104, a projector 108, an imaging camera 110, a look-up table storing information for uniquely identifying a plurality of surgical instruments.

In this type of system, the distance-measuring device measures the distance and/or contour/topology of the object onto which the augmented information is projected. The imaging camera captures images of the surgical devices, compares the captured images with the information stored in the look-up table to identify surgical instruments and their location/orientation relative to the object.

The surgical tool may be provided with a fiducial to facilitate identification and position tracking of the tool. The fiducial may be produced with visible light spectrum or with IR fluorescent ink. Fiducials can also be constructed with other technologies, such as reflectors.

According to this embodiment, the position of the instruments is tracked with the imaging camera 110 and augmented data in the form of guidance information is projected 108 onto the object (patient), aiding the user with properly positioning the surgical tool. The augmented information may include an image displayed either directly on the tool or next to the tool by the projector providing real time feedback on how to reposition the tool, for example.

In each of the augmented imaging systems described herein, the system assesses the distance to the object and the skew angle between the imaging camera/projector and the physical object and is therefore able to project various messages to the user. For example, if the camera/projector is too low or too high, a message or image can be projected to assist the user with positioning. This can also be applied when the depth sensing camera/projector is scanning an object.

The rest of the system 300 operates the same as the structured light embodiment, and may include any combination of lights 116A, 116B, 116C and 117.

Endoscope with Distance Measurement and Scaling

Figure 4:
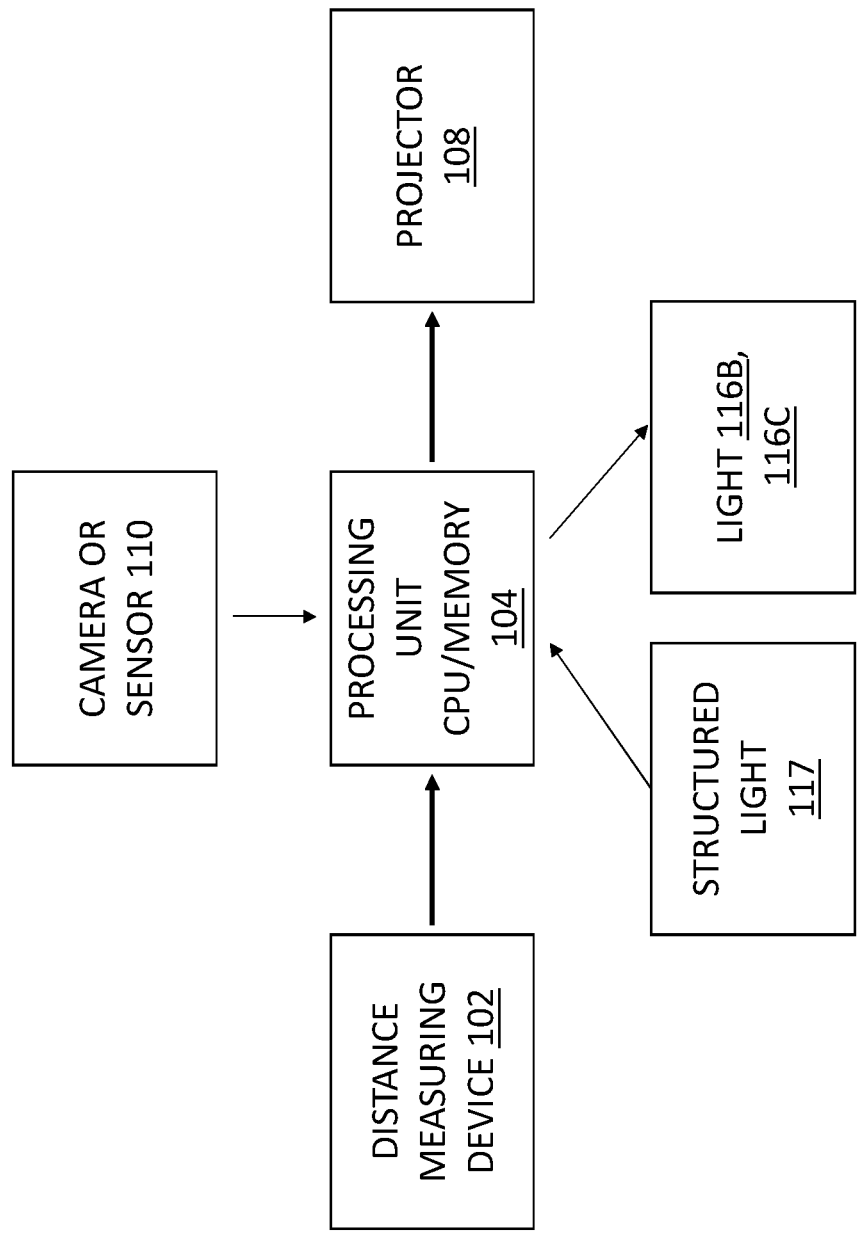
FIG. 4 shows a block diagram of an endoscopic system.

For endoscopic fluorescence imaging applications it would be desirable to determine the distance between the distal end of the endoscope and the fluorescent target. FIG. 4 is a block diagram of an endoscopic system 400 that utilizes the assessed distance to optimize the intensity of fluorescent emission. A distance-measuring device 102 or the structured light source 117 and camera sensor 110 can be utilized, for example, to automatically adjust the intensity of the projector 108 or lights 116B/116C used for excitation.

The distance-measuring device 102 (or structured light source 117, or projector 108) may operate through the endoscope tube and measure the distance from the distal end of the endoscope to the surgical site. Alternatively, the distance measurement assessment could be accomplished through separate optics than those of the endoscope. Distance can be measured, for example, by using structured light 117 and an additional camera/sensor 110 that is separate from the endoscope camera. This alternative may prove to be beneficial in that the pattern or signal used for distance sensing is not distorted by the endoscope optics.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. An imaging system projecting augmented information on a physical object, the imaging system comprising:
   a processor;
   a memory device operably connected to the processor, the memory device storing augmented image information;
   a projector operably coupled to the processor, the processor configured to project augmented image information onto the physical object;
   a distance-measuring device operably connected to the processor and configured to measure a distance to the physical object; and
   an inertial measurement unit ably connected to the processor,
   wherein the processor is configured to:
      use distance measurement information from the distance-measuring device to adjust scaling of the augmented image information,
      provide the scale adjusted augmented image information to the projector, and
      disable the distance-measuring device from making distance measurements responsive to at least one condition selected from a group consisting of: (i) the inertial measurement unit detecting that the imaging system is stationary for at least a predefined amount of time, (ii) the inertial measurement unit detecting that a position of the imaging system moves more than a predefined threshold amount, and (iii) the inertial measurement unit detecting that an orientation of the imaging system changes from more than a predefined threshold amount.

2. The imaging system of claim 1, wherein the distance-measuring device is selected from the group consisting of laser range finder, laser scanning, time of flight, structured light, light field camera, and acoustic measurement device.

3. The imaging system of claim 1, wherein the distance-measuring device is configured to determine at least one of a topology of the physical object and an orientation of the physical object relative to the distance-measuring device, and
   wherein the processor is further configured to use at least one of the topology and the orientation to adjust scaling of the augmented information.

4. The imaging system of claim 1, further comprising at least one light source selected from the group consisting of structured light, background infrared light, visible light, and fluorophore excitation light.

5. The imaging system of claim 1, wherein the distance-measuring device comprises:
   at least one of a sensor and a camera operably connected to the processor,
   wherein the projector is configured to project a predefined light pattern onto the physical object in at least one of a visible and an infrared light spectrum,
   wherein the at least one of a sensor and a camera detect a reflectance of the predefined light pattern, and
   wherein the processor is configured to calculate at least one of the distance to the physical object and a topology of the physical object using the detected reflectance.

6. The imaging system of claim 5, wherein the projector projects at least two predefined light patterns onto the physical object and the at least one of a sensor and a camera detect a reflectance of the at least two predefined light patterns and the processor calculates at least one of the distance to the physical object and a topology of the physical object using the detected reflectance.

7. The imaging system of claim 5, wherein the at least one of a sensor and a camera are further configured to detect a location of a fiducial attached to or painted onto the physical object, the fiducial being visible in either a visible light spectrum or an infrared spectrum, the processor using the location of the fiducial to register the augmented image information with the physical object.

8. The imaging system of claim 1, wherein the distance-measuring device comprises a time of flight sensor unit including a light source and a light sensor.

9. The imaging system of claim 8, wherein the light source is an infrared light source and the light sensor is configured to detect infrared light.

10. The imaging system of claim 1, wherein the distance-measuring device comprises:
    at least one of a sensor and a camera operably connected to the processor; and
    a second projector, said second projector configured to project at least one predefined structured light pattern in either a visible or infrared spectrum onto the physical object,
    wherein the at least one of the sensor and the camera detect a reflectance of the predefined light pattern, and
    wherein the processor is configured to:
       calculate at least one of the distance to the physical object and a topology of the physical object using the detected reflectance,
       use at least one of the distance or the topology to adjust scaling of the augmented information, and
       provide the scale adjusted augmented information to the projector.

11. The imaging system of claim 10, wherein the at least one of a sensor and a camera are further configured to detect a location of a fiducial attached to or painted onto the physical object, the fiducial being visible in either a visible light spectrum or an infrared spectrum, the processor using the location of the fiducial to register the augmented image information with the physical object.

12. The imaging system of claim 1, wherein the processor is configured to trigger the projector to display an alert responsive to: (i) the imaging system being not oriented within predefined threshold, or (ii) the measured distance to the physical object exceeding a predefined threshold distance.

13. An imaging system projecting augmented information on a physical object, the imaging system comprising:
a processor;
a memory device operably connected to the processor, the memory device storing augmented image information;
a projector operably coupled to the processor, the processor configured to project augmented image information onto the physical object;
a distance-measuring device operably connected to the processor and configured to measure a distance to the physical object;
a light; and
an inertial measurement unit operably connected to the processor,
wherein the processor is configured to:
use distance measurement information from the distance-measuring device to adjust scaling of the augmented image information,
provide the scale adjusted augmented image information to the projector,
disable the light responsive to at least one condition selected from a group consisting of: (i) the inertial measurement unit detecting that the imaging system is moving more than predefined threshold amount and (ii) the inertial measurement unit detecting that an orientation of the imaging system changes from more than a predefined threshold amount.

14. The imaging system of claim 1, further comprising:
at least one of a camera or a sensor operably connected to the processor and configured to detect a fluorescent emission,
wherein the processor is configured to cause the projector to project light to excite fluorophores in or on the physical object, and
wherein the at least one of the camera or the sensor is configured to detect a fluorescent emission of the fluorophores, and
wherein the processor is configured to store the detected fluorescent emission in the memory as augmented image information.

15. The imaging system of claim 14, wherein the projector is configured to project the augmented image information onto the physical object using light in the visible spectrum.

16. The imaging system of claim 14, wherein the projector has a first mode for projecting augmented image information on the physical object, and second mode for projecting light to excite fluorophores in or on the physical object.

17. The imaging system of claim 16, wherein the projector has a third mode for projecting a predefined light pattern.

18. The imaging system of claim 1, further comprising:
at least one of a camera or a sensor operably connected to the processor and configured to detect a fluorescent emission; and
at least one of a light source and a second projector configured to project light onto the physical object,
wherein the processor is configured to cause the at least one of the light source and the second projector to project light to excite fluorophores in or on the physical object, and
wherein the at least one of the camera or the sensor is configured to detect a fluorescent emission of the fluorophores, and
wherein the processor is configured to store the detected fluorescent emission in the memory as augmented image information.

19. The imaging system of claim 18, wherein the processor is configured to trigger the projector to display an alert if an intensity of the detected fluorescence is below a threshold value.

20. The imaging system of claim 1, further comprising:
at least one of a camera or a sensor operably connected to the processor; and
a second projector operably connected to the processor and configured to project a virtual fiducial in either an infrared light or a visible light spectrum onto the physical object,
wherein the processor is configured to cause the second projector to project the virtual fiducial on the physical object,
wherein the at least one of the camera or the sensor is configured to detect a location of the virtual fiducial, and
wherein the processor is configured to use the location of the virtual fiducial to register the augmented image information with the physical object.

21. The imaging system of claim 1, further comprising:
at least one of a camera or a sensor operably connected to the processor and configured to detect fluorescent emission,
wherein the processor is configured to cause the projector to project light to excite fluorophores in or on the physical object, and
wherein the at least one of the camera or the sensor is configured to detect a fluorescent emission of the fluorophores in a first wavelength,
wherein the processor is configured to store the detected fluorescent emission in the memory as augmented image information and trigger the projector to project the augmented image information onto the physical object in a second wavelength different from the first wavelength.

22. The imaging system of claim 13, wherein the projector is configured to project the augmented image information onto the physical object using light in the visible spectrum.

23. The imaging system of claim 13, wherein the distance-measuring device is selected from the group consisting of laser range finder, laser scanning, time of flight, structured light, light field camera, and acoustic measurement device.

* * * * *